(12) United States Patent
Hoshino et al.

(10) Patent No.: US 6,993,113 B2
(45) Date of Patent: Jan. 31, 2006

(54) METHOD OF EVALUATING ION-EXCHANGE FILM, METHOD OF EVALUATING ORGANIC SAMPLE AND X-RAY MEASURING APPARATUS

(75) Inventors: Kazuhito Hoshino, Saitama (JP); Yoshio Iwasaki, Tokyo (JP)

(73) Assignee: Rigaku Corporation, Akishima (JP)

( * ) Notice: Subject to any disclaimer, the term of this patent is extended or adjusted under 35 U.S.C. 154(b) by 35 days.

(21) Appl. No.: 10/457,354

(22) Filed: Jun. 10, 2003

(65) Prior Publication Data

US 2004/0008816 A1   Jan. 15, 2004

(30) Foreign Application Priority Data

Jun. 19, 2002   (JP)   ............................. 2002-178360

(51) Int. Cl.
*G01N 23/201*   (2006.01)
*G01N 23/20*   (2006.01)

(52) U.S. Cl. ............................ 378/86; 378/70; 378/88; 378/79

(58) Field of Classification Search ................. 378/70, 378/80, 81, 86, 87, 88, 89, 90, 7, 50, 53, 378/79
See application file for complete search history.

(56) References Cited

U.S. PATENT DOCUMENTS

| | | | | |
|---|---|---|---|---|
| 5,805,662 A | * | 9/1998 | Kurbatov et al. | ............. 378/87 |
| 6,011,074 A | * | 1/2000 | Sorenson et al. | ............. 521/26 |
| 6,054,710 A | * | 4/2000 | Bruggeman | ................. 250/307 |
| 6,330,301 B1 | * | 12/2001 | Jiang | ........................... 378/85 |
| 6,504,902 B2 | | 1/2003 | Iwasaki et al. | |

FOREIGN PATENT DOCUMENTS

JP   2001-356197 A   12/2001

OTHER PUBLICATIONS

J.A. Elliott et al., "Interpretation of the Small-Angle X-ray Scattering from Swollen and Oriented Perfluorinated Ionomer Membranes," MACROMOLECULES 2000, vol. 33, No. 11, 2000, American Chemical Society, Washington, D.C., pp. 4161-4171.

Abstract of Soviet Union Patent No. 1582097, Crystallography DES, Jul. 30, 1990, from Database WPI, Section E1, Week 199113, AN 1991-093510, Derwent Publications Ltd., London, GB.

A. Okawara et al., Real-time analysis of small-angle X-Ray scattering from perfluorocarboxylic ionomer membranes during electrodialysis, POLYMER, 1992, vol. 33, No. 8, Elsevier, pp. 1579-1582.

(Continued)

Primary Examiner—Edward J. Glick
Assistant Examiner—Irakli Kiknadze
(74) Attorney, Agent, or Firm—Buchanan Ingersoll PC

(57) ABSTRACT

Disclosed herein is a method of evaluating the performance of an ion-exchange film. In the method, small-angle scattering curves for the ion-exchange film are obtained by an X-ray measuring apparatus that can detect X-rays scattered at small angles with respect to the axis of an X-ray applied to film. From the positions of the peaks on the small-angle scattering curves and the X-ray intensities at these peaks, the molecular structure of the ion-exchange film is determined, thereby to evaluate the performance of the ion-exchange film.

22 Claims, 11 Drawing Sheets

OTHER PUBLICATIONS

T.D. Gierke et al., "The Morphology in Nafion Perfluorinated Membrane Products, as Determined by Wide- and Small-Angle X-ray Studies," Journal of Polymer Science: Polymer Physics Edition, 1981, vol. 19, No. 11, John Wiley & Sons, Inc., New York, pp. 1687-1704.

G. Gebel, "Structural evolution of water swollen perfluorosulfonated ionomers from dry membrane to solution," Polymer, Jul. 2000, vol. 41, No. 15, Elsevier Science Publishers B.V., GB, pp. 5829-5838.

R. Mosdale et al., "Water profile determination in a running proton exchange membrane fuel cell using small-angle neutron scattering," Journal of Membrane Science, Sep. 18, 1996, vol. 118, No. 2, Elsevier Scientific Publ. Company, Amsterdam, NL, pp. 269-277.

P.J. James et al, "In situ rehydration of perfluroosulphonate ion-exchange membrane studied by AFM", POLYMER, May 2000, vol. 41, No. 11, Elsevier Science Publishers, B.V., GB, pp. 4223-4231.

Copending U.S. Appl. No. 10/456,508, filed Jun. 9, 2003, Kazuhito Hoshino et al.

K. Jokela et al., "Temperature-Dependent X-ray Scattering Studies on Radiation Grafted and Sulfonated Poly (Vinylidene Fluoride)", Materials Science Forum, vols. 321-324, 2000, pp. 481-486, Trans Tech Publications, Switzerland.

* cited by examiner

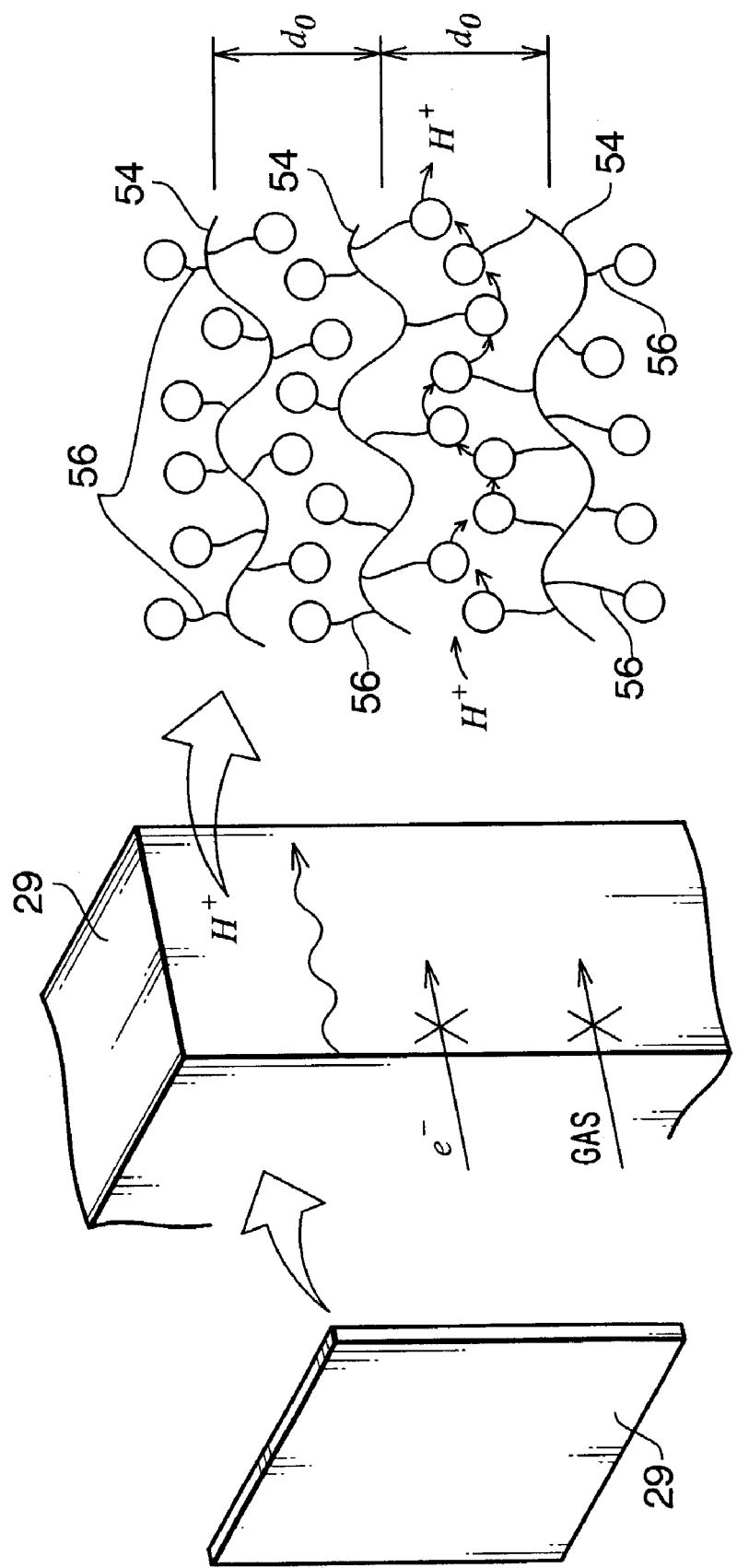

METHOD OF EVALUATING ION-EXCHANGE FILM, METHOD OF EVALUATING ORGANIC SAMPLE AND X-RAY MEASURING APPARATUS

BACKGROUND OF THE INVENTION

1. Field of the Invention

The present invention relates to a method of evaluating the performance of organic samples, such as ion-exchange film. The invention also relates to an X-ray measuring apparatus that is fit for use in this method.

2. Description of the Related Art

Recently, various apparatuses including macromolecular organic materials are provided in the industry. In the field of fuel cells, for example, the main component of the fuel cell is ion-exchange film that is made of macromolecular organic material. As FIG. 11 shows, the fuel cell comprises a pair of electrodes, or fuel pole 51 and air pole 52, and an ion-exchange film 29 interposed between the poles 51 and 52. Hydrogen ($H_2$), i.e., the fuel, is supplied through the fuel pole 51 to the ion-exchange film 29. Also, Oxygen ($O_2$) is supplied through the air pole 52 to the ion-exchange film 29.

In the fuel cell, hydrogen and oxygen undergo the following chemical reaction:

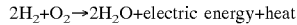

$$2H_2 + O_2 \rightarrow 2H_2O + \text{electric energy} + \text{heat}$$

This is a chemical reaction that is invert to the electrolysis of water. The reaction yields electric energy. The heat generated along with the electric energy can be absorbed by an appropriate cooling method in which the cooling water is circulated.

The ion-exchange film 29 used in the fuel cell has been made by synthesizing straight chains 54 and side chains 56. The straight chains 54 are spaced from one another at interval d0. The side chains 56 branch from the straight chains 54. In Nafion (registered trademark of E.I. du Pont de Nemours and Co.) known widely as an ion-exchange film, the straight chains 54 and the side chains 56 have such molecular structures as specified in FIG. 10.

In these molecular structures, the straight chains 54 are Teflon (registered trademark) groups and the side chains 56 are those formed by combining functional groups. Some of the functional groups shown in FIG. 10 may be removed or substituted by other functional groups, or other functional groups may be added, to alter the molecular structure of the ion-exchange film. The performance of the ion-exchange film can thereby be changed in various ways.

Having this specific molecular structure, the ion-exchange film 29 allows the passage of protons $H^+$ and does not allow the passage of electrons $e^-$ and gas, as illustrated in FIG. 9B. Namely, the film 29 performs ion exchange. The higher the ion-exchanging performance, the higher the performance of the fuel cell. The ion-exchanging performance is considered to change in accordance with the molecular structure shown in FIG. 9C. Specifically, it is influenced by the interval d0 between the straight chains, the arrangement of the side chains 56, and the like.

Hence, it is recommended that the molecular structure of ion-exchange film or the like, which is made of macromolecular organic material, be determined in order to evaluate performance of the macromolecular organic material. Methods of determining the molecular structures of macromolecular organic materials are known. Among these methods are the NMR-measuring method and the IR-measuring method. In the NMR method, an NMR (Nuclear Magnetic Resonance) spectrometer is employed. In the IR method, an IR (Infrared) spectrophotometer is used.

The NMR-measuring method utilizes the phenomenon called "nuclear magnetic resonance," in which the amplitude of magnetic moment changes when an electromagnetic wave is applied to an atom whose nuclear has magnetic moment, in order to determine the molecular structure, etc. of a sample. The IR-measuring method determines the molecular structure, etc. of a sample, from the infrared absorption spectrum, i.e., the relation between the intensity of the infrared beam passing the sample (plotted on the ordinate) and the wavelength of the infrared beam (plotted on the abscissa).

With the NMR-measuring method and the IR-measuring method, however, it is difficult to obtain reliable evaluation of the sample, by using a measuring apparatus of simple configuration. Further, they cannot determine the molecular structure of macromolecular organic materials such as ion-exchange film, while maintaining the materials at such high humidity and such high temperature as they are set when they are used in practice. This is why macromolecular organic materials, such as ion-exchange film, are not evaluated by means of in-situ measuring at present. In other words, the materials are not evaluated for their molecular structures in the very conditions they are used.

SUMMARY OF THE INVENTION

The present invention has been made in view of the foregoing. An object of the invention is to provide a method that can reliably accurately determine the molecular structure of macromolecular organic materials, such as ion-exchange film, by using apparatus that are widely and generally employed.

To achieve the object, a method of evaluating the performance of an ion-exchange film, according to the present invention, comprises the step of obtaining small-angle scattering curves for the ion-exchange film, by means of an X-ray measuring apparatus which is configured to detect X-rays scattered at small angles with respect to the axis of an X-ray applied to the ion-exchange film.

The small-angle scattering curves are curves G that are shown in FIG. 7. Each curve G is formed by plotting the scattering angle (2θ) on the abscissa, and the X-ray intensity on the ordinate, as seen from FIG. 7.

This method of evaluating the ion-exchange film can reliably determine the molecular structure of the ion-exchange film, merely by using an ordinary X-ray measuring apparatus that is widely and generally employed. The X-ray measuring apparatus is more versatile than the NMR-measuring apparatus and the IR-measuring apparatus, in respect of the installation of additional devices for the sample. Thus, the method can determine the molecular structure of the sample in the same conditions as the sample is actually used.

It is desired that the method of evaluating an ion-exchange film, described above, should further comprise the steps of: obtaining small-angle scattering curves for a plurality of ion-exchange films; and finding a difference between the positions of peaks on the small-angle scattering curves and/or a difference between the X-ray intensities at the peaks.

The difference between the positions of peaks on the small-angle scattering curves for a plurality of ion-exchange films may be obtained. Then, the molecular structures of the respective films can be determined. From the molecular structures of the films, the difference in performance between the ion-exchange films can be evaluated.

Further, once the positions of the peaks on the small-angle scattering curves for a plurality of ion-exchange films are determined, it is possible to verify the number of side chains and the regularity of the molecular structure of each ion-exchange film. Thus, the difference in performance between the ion-exchange films can be evaluated.

It is desired that the method of evaluating an ion-exchange film, described above, should further comprise the steps of: obtaining small-angle scattering curves for one ion-exchange film, while the film remains in a different condition; and finding the difference between the positions of peaks on the small-angle scattering curves and/or the difference between the X-ray intensities at the peaks.

Each small-angle X-ray scattering curve is obtained while the film remains in a specific condition. Further, the difference between the positions of peaks on the small-angle scattering curves and/or the difference between the X-ray intensities at the peaks are determined. This makes it possible to evaluate the different ion-exchanging abilities that the film has in different conditions.

Once the difference between the X-ray intensities at the peaks on the small-angle X-ray scattering curves for a plurality of ion-exchange films are determined, it is possible to verify the number of side chains in the molecular structure of each film and the regularity of the molecular structure. Then, the difference in performance between the ion-exchange films can be evaluated.

In the method of evaluating an ion-exchange film, described above, it is desired that the step of obtaining small-angle scattering curves be performed while the ion-exchange film remains held in a watertight sample chamber, together with liquid.

Then, the measuring can be carried out while the ion-exchange film remains immersed in water and, thus, wetted at humidity of 100%. The liquid may be water. The ion-exchange film remains wetted water all time when it is used as a component in a fuel cell. Since the ion-exchange film remains wetted while being measured, it can be evaluated in the same condition it is used in practice.

In the method of evaluating an ion-exchange film, described above, it is desired that the temperature in the sample chamber be adjusted while the film is being measured. The ion-exchange film is wetted and generates much heat, while it is being used. Since the film is measured while the temperature in the sample chamber is being adjusted, it can be evaluated in the same condition it is used in practice.

If the temperature in the sample chamber is adjusted, it should be adjusted to the very value at which the ion-exchange film is used in practice.

The temperature in the sample chamber can be adjusted to a value ranging from room temperature to a higher temperature but less than 100° C. In particular, the temperature can be adjusted to a value ranging from 80° C. to 90° C. If the temperature is the very temperature at which the ion-exchange film is used in practice or close thereto, the film can be measured in the condition it is actually used.

In the method of evaluating an ion-exchange film, described above, it is desired that the step of obtaining small-angle scattering curves should have a step of obtaining a two-dimensional scattering profile pertaining to the ion-exchange film, by using a two-dimensional X-ray detector.

The two-dimensional X-ray detector is of the type that receives X-rays in a plane and detects X-rays at any points in the plane. It may be an X-ray detector having an X-ray dry plate or X-ray film, or may be an X-ray detector having a storage phosphor. Alternatively, it may be an X-ray detector that incorporates a planer CCD (i.e., Charge Coupled Device) sensor.

Storage phosphor is energy-accumulating phosphor. It is made by applying fine crystals of super-luminance material such as $BaFBr:Er^{2+}$ on the surface of a flexible film, plate-like film or any other member. The storage phosphor can store electromagnetic waves such as X-rays, in the form of energy. When irradiated with intense exciting light such as a laser beam, the storage phosphor releases the energy in the form of light.

That is, when X-rays or the like is applied to the storage phosphor, energy is accumulated as a latent image in that part of the storage phosphor which has been irradiated with the X-rays. When the storage phosphor is irradiated with a laser beam or the like, it releases the energy of the latent image in the form of light. The light released may be detected by a photoelectric transducer such as a photoelectric tube. Thus, the diffraction angle and intensity of the X-rays that have formed the latent image can be measured.

The CCD sensor is an electronic element known in the art. It is an X-ray detector that comprises CCDs (i.e., Charge Coupled Devices) arranged in a row or in a planar matrix. The CCD sensor has a plurality of electrodes on an insulating layer that is provided on, for example, a silicon substrate. The electrodes are arranged in a row or in rows and columns, thus forming an electrode array. The CCD sensor is constructed by arranging the electrode array correspondingly for portions for receiving X-rays.

When X-rays are applied to the respective electrodes of the array, an electric charge is accumulated beneath each electrode. When a voltage is applied between the electrode and the substrate, the electric charge is transferred in the CCD sensor until it is output from the CCD sensor. Thus, the CCD sensor can detect the positions where the X-rays have applied to the electrodes and the intensities of the X-rays, almost at the same time.

The two-dimensional scattering profile is such a two-dimensional image as shown in FIG. 8A or FIG. 8B. These images are formed on the X-ray receiving surface of the two-dimensional X-ray detector. The small-angle scattering curves G shown in FIG. 7 are obtained by plotting values in the graph. Each of these values has been acquired by integrating the regions for the same scattering angle ($2\theta$), which exist in the two-dimensional scattering profile E shown in FIG. 8A or 8B.

In the method of evaluating an ion-exchange film, described above, it is desirable that the X-ray measuring apparatus should have an X-ray focusing means which is arranged on a propagation path of the X-ray applied to the ion-exchange film. Note that the X-ray focusing means is an X-ray optical element that can focus an X-ray diverging while propagating, at a downstream point. The X-ray focusing element may be, for example, a con-focal mirror that utilizes the reflection of the X-ray, or an X-ray focusing element that makes use of the diffraction of the X-ray.

In any X-ray optical system of ordinary type that has no X-ray focusing means, the X-rays applied to an ion-exchange film, or the sample, have low intensity. An X-ray focusing means, if used as in the method described above, can focus an X-ray, intensifying the X-ray. Thus, a high-intensity X-ray can be applied to the ion-exchange film in the method according to this invention.

Any X-ray measuring apparatus of the ordinary structure, wherein the X-rays used have low intensity. Therefore, it needs a very long time to obtain such a two-dimensional scattering profile E as shown in FIG. 8A or 8B and, hence, to obtain such small-angle scattering curves G as illustrated in FIG. 7. By contrast, the X-ray measuring apparatus described above can obtain a two-dimensional scattering profile E within a very short time, because it comprises the X-ray focusing means that can apply a high-intensity X-ray to the ion-exchange film. This helps to perform in-situ measuring on the ion-exchange film.

Assume that the ion-exchange film immersed in liquid, for example, water, is thereby wetted, and is heated to a high temperature such as 90° C., whereby the film is subjected to the in-situ measuring. Water quickly changes in state, or is vaporize, at the temperature of 90° C. Hence, the ion-exchange film cannot be subjected to the in-situ measuring if it takes a long time to measure the small-angle scattering of X-rays.

In the method of evaluating an ion-exchange film, described above, the ion-exchange film can be irradiated with a high-intensity X-ray. The method can reliably evaluate ion-exchange films that can remain in the same condition, but for a very short time.

In the method of evaluating an ion-exchange film, described above, it is desired that the X-ray focusing means be a con-focal mirror. Note that a con-focal mirror is an X-ray reflecting mirror that has at least two X-ray reflecting surfaces intersecting with each other at right angles. The mirror is so designed that the X-rays reflected from the X-ray reflecting surfaces meet at the same focal point.

In any X-ray optical system of ordinary type that has no X-ray focusing means, the X-rays applied to an ion-exchange film have low intensity. A con-focal mirror, if used as in the optical system, can focus an X-ray. Then, a high-intensity X-ray can be applied to the sample, i.e., ion-exchange film.

In any X-ray measuring apparatus of the ordinary structure, wherein the X-rays used have low intensity, a very long time, e.g., 15 hours to 30 hours, is required to obtain such a two-dimensional scattering profile E as shown in FIG. 8A or 8B and, hence, to obtain such small-angle scattering curves G as illustrated in FIG. 7. By contrast, the X-ray measuring apparatus described above can obtain a two-dimensional scattering profile E within a very short time, for example, 20 minutes to one hour, because it comprises a con-focal mirror that can apply a high-intensity X-ray to the ion-exchange film. This helps to perform in-situ measuring on the ion-exchange film.

In the method of evaluating an ion-exchange film, which comprises X-ray focusing means, it is desired that the X-ray measuring apparatus should further have a point-focus X-ray source.

The term "point focus" is used in contrast to "line focus." "Point focus" pertains to X-rays that have a square cross section having four sides of substantially the same length, forming a square light spot on the sample. By contrast, the term "line focus" pertains to X-rays that have a rectangular cross section, thus forming an elongated light spot on the sample. The point-focus X-ray source emits X-ray beams, each forming, on the sample, a circular light spot having a diameter of, for example, about 0.3 mm or a square light spot having a size of about 0.3 mm×about 0.3 mm.

If a line-focus X-ray source is used, those parts of the rectangular light spot which lie outside each tiny light-receiving region of the ion-exchange film will be wasted, not contributing to the measuring of the X-ray. This means that the line-focus X-ray source cannot apply sufficiently intense X-rays to the ion-exchange film. By contrast, any X-ray emitted from the point-focus X-ray source is applied, in its entirety, to one tiny light-receiving region of the ion-exchange film. Thus, the point-focus X-ray source can apply sufficiently intense X-rays to the ion-exchange film.

A method of evaluating the performance of an organic sample, according to the present invention, comprises the step of obtaining small-angle scattering curves for the organic sample, by means of an X-ray measuring apparatus which is configured to detect X-rays scattered at small angles with respect to the axis of an X-ray applied to the organic sample. Note that the organic sample may be a drug, a genome-pharmaceutical substance, a synthesized compound, or the like, to say nothing of an ion-exchange film.

This method of evaluating an organic sample can accurately determine the molecular structure of the organic sample, merely by using an X-ray measuring apparatus that is generally and widely used. Further, the method can analyze the molecular structure of the organic sample in the same conditions as the sample is actually used. This is because the X-ray measuring apparatus is more versatile than the NMR-measuring apparatus and the IR-measuring apparatus, in respect of the installation of additional devices for the sample.

It is desired that the method of evaluating an organic sample, described above, should comprise the step of obtaining small-angle scattering curves for a plurality of organic samples, and the step of finding a difference between the positions of peaks on the small-angle scattering curves and/or a difference between the X-ray intensities at the peaks.

Once the difference in the peak positions on the small-angle scattering curves, between organic samples is obtained, the molecular structures of the samples can be analyzed. Then, the difference in characteristic between the organic samples can be evaluated. If the difference in X-ray intensities at the peaks, between the organic samples, is obtained, it will be possible to verifying the number of side chains and the regularity of the molecular structure. In this case, too, the difference in characteristic between the samples can be evaluated.

It is desired that the method of evaluating an organic sample, described above, should further comprise the steps of: obtaining small-angle scattering curves for one organic sample, while the sample remains in a different condition; and finding the difference between the positions of peaks on the small-angle scattering curves and/or the X-ray intensities at the peaks.

Each small-angle X-ray scattering curve is obtained while the organic sample remains in a specific condition. Further, the difference between the positions of peaks on the small-angle scattering curves and/or the X-ray intensities at the peaks are determined. This makes it possible to evaluate the different ion-exchanging abilities that the organic sample has in different conditions. Once the difference between the X-ray intensities at the peaks on the small-angle X-ray scattering curves for a plurality of organic samples are determined, it is possible to verify the number of side chains in the molecular structure of each sample and the regularity of the molecular structure. In this case, the difference in characteristic between the samples can be evaluated.

In the method of evaluating an organic sample, described above, it is desired that the step of obtaining small-angle scattering curves be performed while the sample remains held in a watertight sample chamber, together with liquid. Then, the measuring can be carried out while the organic sample remains immersed in water and, thus, wetted. The liquid may be water. Since the organic sample remains wetted while being measured, it can be evaluated in the same condition it is used in practice.

In the method of evaluating an organic sample, described above, it is desired that the temperature in the sample chamber be adjusted while the organic sample is being measured.

If the temperature in the sample chamber is adjusted, it should be adjusted to the very value at which the organic sample is used in practice. This makes it possible to evaluate the organic sample while it remains in the same condition it is used in practice.

In the method of evaluating an organic sample, described above, it is desired that the step of obtaining the small-angle scattering curves should have the step of obtaining a two-dimensional scattering profile pertaining to the organic sample, by using a two-dimensional X-ray detector.

In the method of evaluating an organic sample, described above, it is desired that the X-ray measuring apparatus has an X-ray focusing means which is arranged on a propagation path of the X-ray applied to the organic sample. Then, the organic sample can be irradiated with high-intensity X-rays, thanks to the use of the X-ray focusing means. This renders it possible to obtain a two-dimensional scattering profile E pertaining to the organic sample, within an extremely short time. This serves very much to accomplish in-situ measuring of the organic sample.

In the method of evaluating an organic sample, described above, the X-ray focusing means may comprise a con-focal mirror. If a con-focal mirror is employed, the X-ray can be focused before it is applied to the organic sample. Then, the organic sample can be irradiated with high-intensity X-rays. As a result, a two-dimensional scattering profile pertaining to the organic sample can be obtained within a very short time. This helps much to accomplish in-situ measuring of the organic sample.

In the method of evaluating an organic sample using the X-ray focusing means, described above, it is desired that the X-ray measuring apparatus should further have a point-focus X-ray source. A point-focus X-ray source emits X-rays, each having a cross section that is almost square. The X-ray focusing means can focus such an X-ray at a tiny light-receiving region of the organic sample. Thus, the point-focus X-ray source can apply sufficiently intense X-rays to the organic sample.

An X-ray measuring apparatus according to the present invention comprises: a small-angle X-ray optical system which is configured to detect X-rays scattered at small angles with respect to the axis of an X-ray applied to a sample; a first storage means for storing small-angle scattering curves obtained by using the small-angle, X-ray optical system; a second storage means for storing small-angle scattering curves for a standard sample; and a display means for displaying the small-angle scattering curves stored in the first storage means and the small-angle scattering curves stored in the second storage means, either at the same time or at different times.

The X-ray measuring apparatus may compare, on the screen of the display means, the small-angle scattering curves pertaining to the sample with the small-angle scattering curves pertaining to the standard sample. Thus, the difference in characteristic between the sample and the standard sample can be determined easily and quickly.

Another X-ray measuring apparatus according to the present invention comprises: a small-angle X-ray optical system which is configured to detect X-rays scattered at small angles with respect to the axis of an X-ray applied to a sample; means for calculating the positions of peaks on the small-angle scattering curves obtained by using the small-angle X-ray optical system; and means for displaying thus calculated position of peaks together with the small-angle scattering curves. This X-ray measuring apparatus can enable the operator to recognize, easily and correctly, the positions of the peaks on the small-angle scattering curves and, thus, to evaluate the performance of the sample easily and fast.

It is desired that the X-ray measuring apparatuses described above should further comprise a sample chamber that is configured to allow passage of X-rays, to contain liquid in watertight fashion and to hold the sample in the liquid. Then, small-angle X-ray measuring can be performed on the sample while the sample remains wetted.

It is desired that the X-ray measuring apparatuses described above, which has a sample chamber, should further comprise a sample-temperature adjusting means for adjusting the temperature in the sample chamber. This helps to accomplish in-situ measuring of the sample in almost the same condition the sample is used in practice.

BRIEF DESCRIPTION OF THE DRAWINGS

FIG. 9 is a schematic diagram illustrating the molecular structure of ion-exchange film;

DETAILED DESCRIPTION OF THE PREFERRED EMBODIMENTS (First Embodiment)

An embodiment of a method of evaluating ion-exchange film, or an organic sample, according to the present invention and an embodiment of an X-ray measuring apparatus according to the present invention will be described. These are no more than an example of this invention. The invention is not limited to the embodiments.

Figure 1:
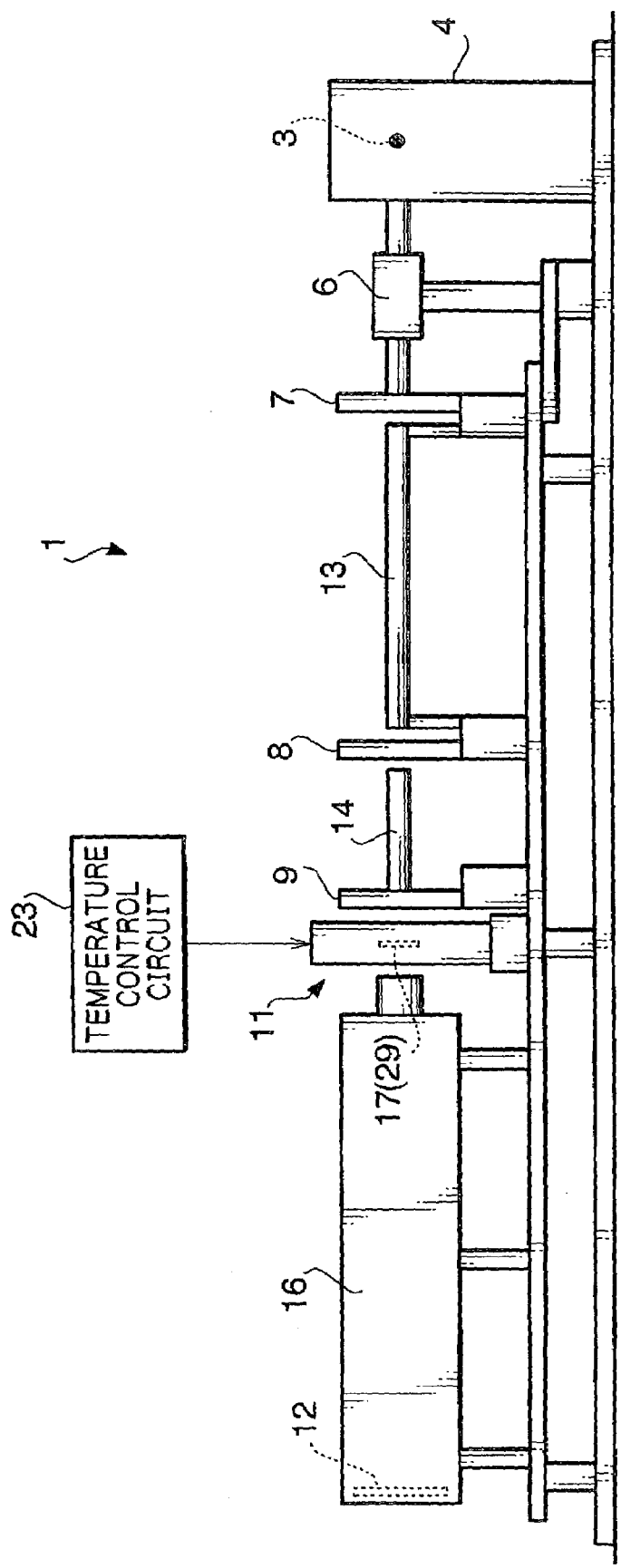
FIG. 1 is a front view of an X-ray small-angle optical device incorporated in an X-ray measuring apparatus according to the present invention.
Figure 2:
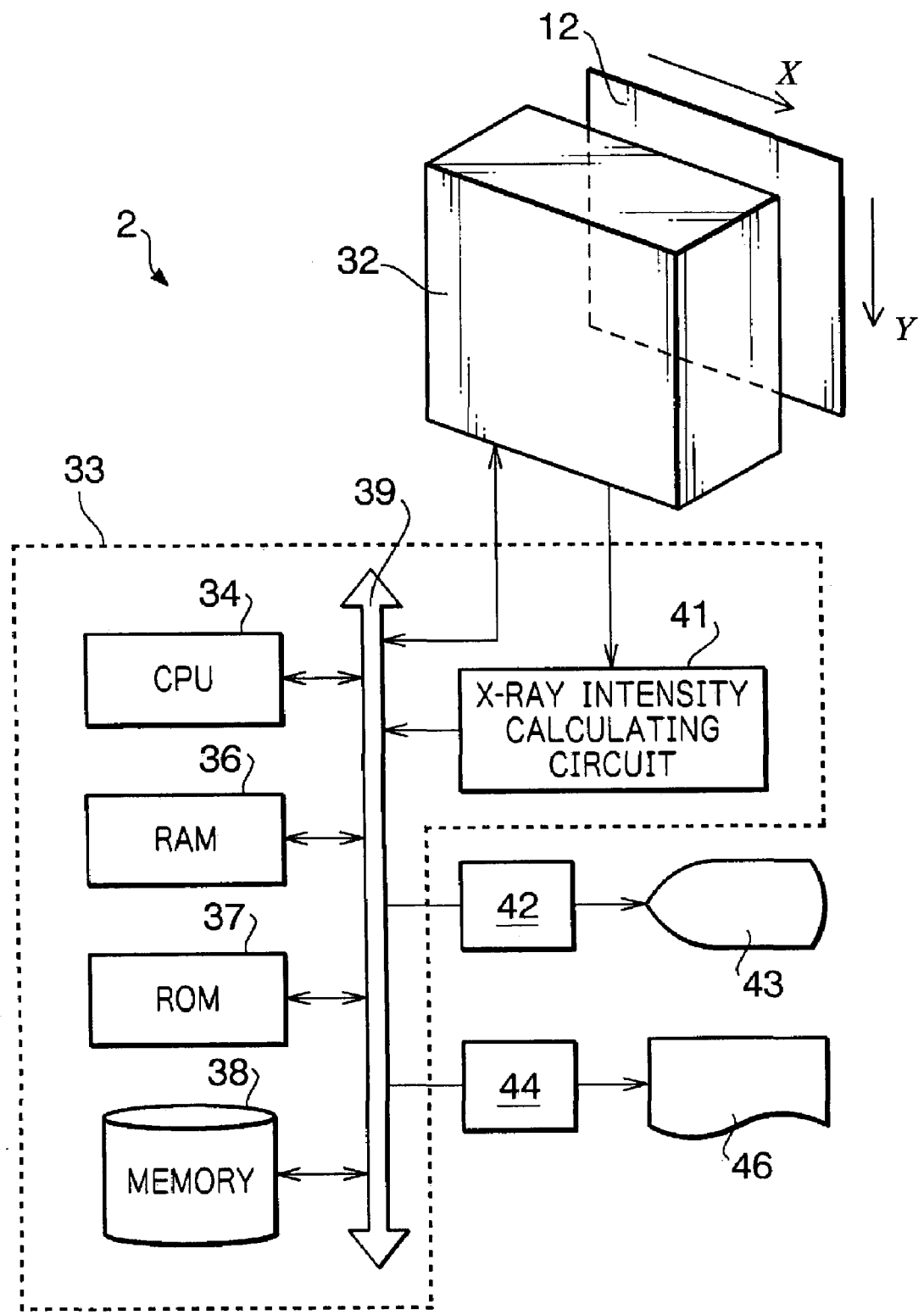
FIG. 2 is a diagram showing a reading device incorporated in the X-ray measuring apparatus according to this invention.

FIG. 1 shows an X-ray small-angle optical device 1 which is one of the components of the X-ray measuring apparatus. FIG. 2 shows a reading device 2 which is another component of the X-ray measuring apparatus. The devices 1 and 2 are installed within a small area that an operator can operate both devices without the necessity of walking a long distance. Note that the X-ray small-angle optical device 1 and the reading device 2 are nothing more than examples of devices that may be used in the present invention to evaluate the ion-exchange film. In other words, they may be replaced by any other devices in the method according to this invention.

As FIG. 1 shows, the X-ray small-angle optical device 1 comprises an X-ray tube 4, a con-focal mirror 6, a first slit 7, a second slit 8, a third slit 9, a sample holder 11, and a two-dimensional X-ray detector 12. The X-ray tube 4 comprises an X-ray source 3. The con-focal mirror 6 is the X-ray focusing means that focuses X-rays generated from the X-ray source 3 at a focal point. The two-dimensional X-ray detector 12 is a phosphor plate that has a storage phosphor layer formed on the X-ray detecting surface.

Figure 3:
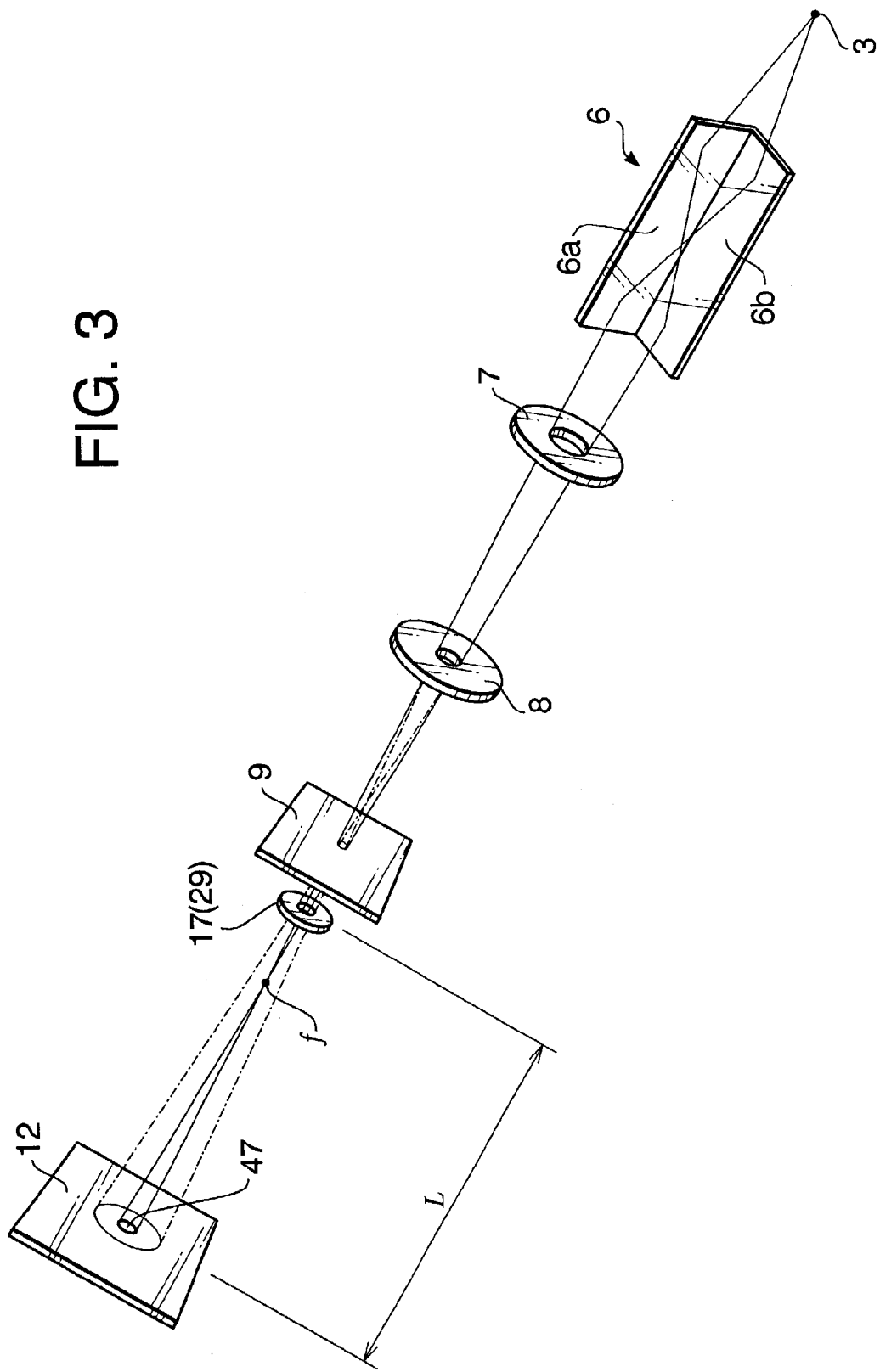
FIG. 3 is a schematic diagram illustrating how an X-ray propagates in the X-ray small-angle optical device shown in FIG. 1.

FIG. 3 is a schematic diagram illustrating how an X-ray propagates in the optical system shown in FIG. 1. In FIG. 3, the components identical to those shown in FIG. 1 are designated at the same reference numerals. As FIG. 3 shows, the con-focal mirror 6 has two X-ray reflecting surfaces 6a and 6b that intersect with each other at right angles. The mirror 6 is an X-ray reflecting mirror that is designed such that the X-rays reflected by the surfaces 6a and 6b reach the same focal point f or points close to one another.

The con-focal mirror 6 may have a single-layer mirror which is made of material that can reflect X-rays, such as nickel, platinum, tungsten, or the like. Alternatively, the mirror 6 may have a multi-layer mirror that has an X-ray reflecting surface and comprises a plurality of thin films laid on the reflecting surface, one upon another. In this case, the mirror 6 reflects X-rays by virtue of the diffraction of X-rays.

As seen from FIG. 1, a tube 13 is arranged between the first slit 7 and the second slit 8, and a tube 14 is provided between the second slit 8 and the third slit 9. Further, a tube 16 is arranged downstream of the sample holder 11 (namely, on the left side of FIG. 1). The two-dimensional X-ray detector 12 is set within one end of the tube 16. The tubes 13, 14 and 16 are connected to a vacuum device and depressurized to a vacuum or almost to a vacuum.

The X-ray small-angle optical device 1 of this embodiment is configured to detect the scattered radiation emanating from the sample 17 held by the sample holder 11. The scattered radiation has a very small intensity. It is therefore necessary to prevent the X-rays scattered by air from disturbing the light beam emanating from the sample 17. To this end, the tubes 13, 14 and 16 are arranged as specified above, thus constituting a vacuum path.

Figure 4:
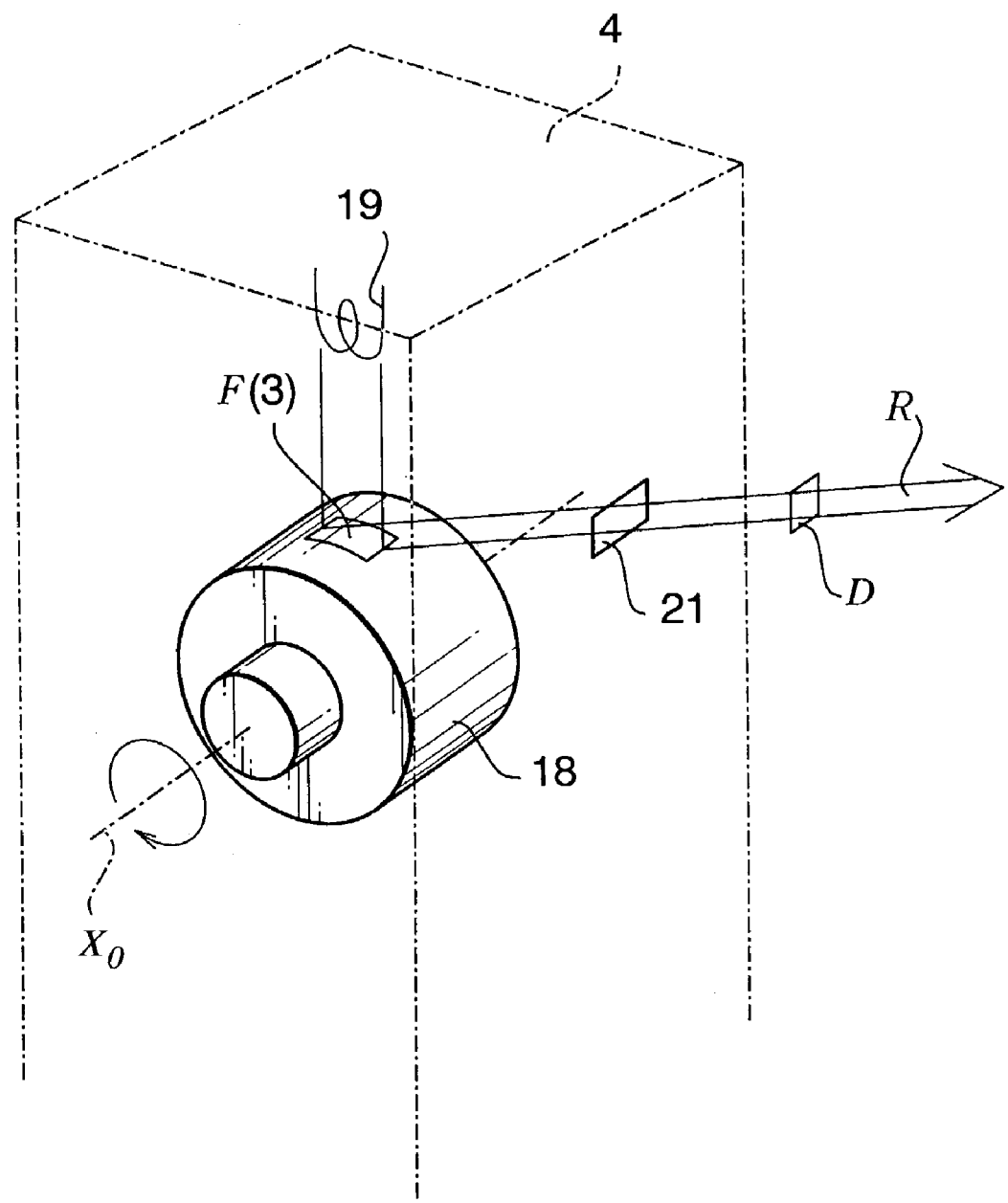
FIG. 4 is a perspective view of an X-ray source that may be used in the X-ray small-angle optical device shown in FIG. 1.

The X-ray tube 4 used in this embodiment should be one that can generate as intense X-rays as possible, so that the sample 17 may be analyzed fast. This is why the X-ray rube 4 comprises a rotor target 18 and a filament 19, as is illustrated in FIG. 4. The rotor target 18 incorporates a cooling unit and can rotate at high speed. The filament 19 can apply a high voltage between it and the target 18.

The filament 19 is heated and emits thermoelectrons when an electric current flows through it. The thermoelectrons emitted from the filament 19 are accelerated, thanks to the high voltage applied between the target 18 and the filament 19. The thermoelectrons thus accelerated impinge upon the surface of the target 18. The region in which the thermoelectrons impinge is an X-ray focus F, at which an X-rays is generated. That is, the X-ray focus F is an X-ray source 3. In the present embodiment, a point-focusing X-ray is picked out from the X-ray source.

The X-ray focus F is rectangular as in most cases. An X-ray is acquired at a short side of the rectangular X-ray focus F in the present embodiment. More precisely, the X-ray is emitted outside the X-ray tube 4 through an X-ray window 21 located at the short side of the X-ray focus F. The X-ray R thus emitted has a cross section that is squared, almost squared, circular, or almost circular. Since the X-ray thus emitted has such a cross section, the X-ray focus F is called "X-ray focus of point type."

The X-ray may be picked out from a long side of the rectangular X-ray focus F. In this case, the X-ray R thus picked out has a rectangular cross section. Hence, the X-ray focus F is called "X-ray focus of line type."

In the present embodiment, the X-ray tube 4 is depressurized to a vacuum or almost a vacuum and the target 18 is rotated at high speed around its axis X0. Further, cooling water is circulated in the target 18. The surface of the target 18 is cooled as the target 18 is rotated at high speed and the cooling water flows in the target 18. This helps to supply many electrons to the X-ray focus F. As a result, an X-ray of high intensity can be generated at the X-ray focus F. The surface of the target 18 may be, for example, a Cu (copper) layer.

The slits provided in the X-ray optical system shown in FIG. 1 may have various shapes, rectangular, circular (i.e., pinhole), and the like. In the present embodiment, the first, second and third slits 7, 8 and 9 are pinholes as shown in FIG. 3. The pinholes are desirable slits since the X-ray source 3 generates a point-focusing X-ray and the mirror 6 is a con-focal mirror in this embodiment.

Figure 5:
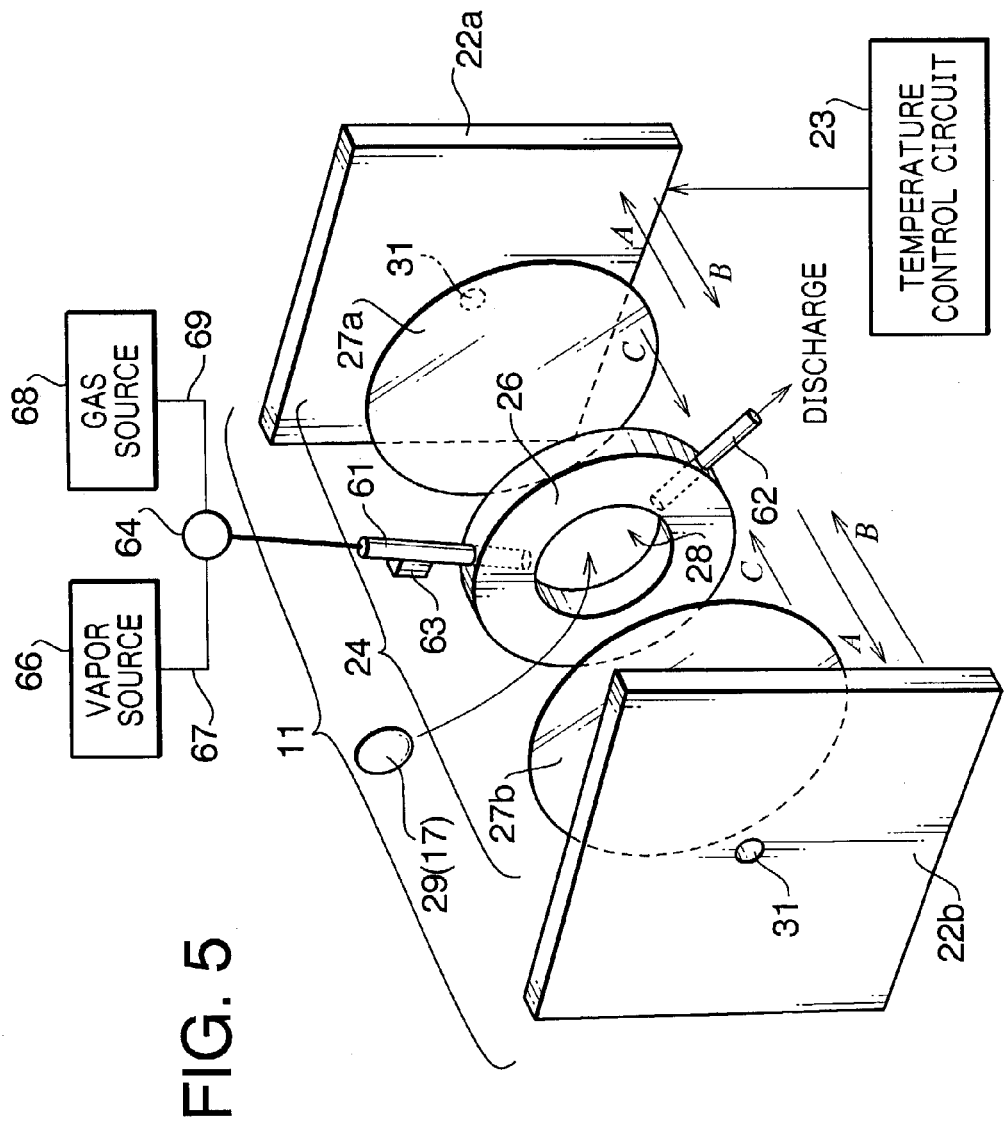
FIG. 5 is an exploded view of an internal structure of the sample holder used in the X-ray small-angle optical device shown in FIG. 1.

As FIG. 5 shows, the sample holder 11 illustrated in FIG. 1 has a pair of heat plates 22a and 22b that function as sample-heating means. The heat plates 22a and 22b can move away from each other in the directions arrows A and toward each other in the direction of arrows B, when driven by an opening-closing mechanism (not shown). The sample-heating means is not limited to the heat plates 22a and 22b. It can be replaced by a sample-heating means of any other structure.

The heat plate 22a or the heat plate 22b, or both contain a member that generates heat when an electric current flows through it. The heat-generating member is, for example, an electric heating wire. The heat-generating member is connected to a temperature control circuit 23. The circuit 23 controls the current supplied to the heat-generating member, thus changing the amount of heat that the heat plate 22a or the heat plate 22b, or both generate. Note that the heat plate 22a or the heat plate 22b, or both have an inner surface that radiates heat.

The heat plates 22a and 22b clamp a sample chamber assembly 24, with their inner surfaces (i.e., heat-radiating surfaces) set in direct contact with the sample chamber assembly 24. Preferably, the heat plates 22a and 22b firmly hold the assembly 24 by using an elastic bias means such as springs, thus preventing the sample chamber assembly 24 from moving.

The sample chamber assembly 24 has a ring-shaped thick member 26 and shields 27a and 27b. The shields 27a and 27b are adhered to the sides of the thick member 26. The thick member 26 is made of, for example, brass and has a thickness of, for example, about 1 mm. The shields 27a and 27b are flexible films and made of material that is transparent to X-rays and exhibits a great mechanical strength. The material may be, for example, polyethylene terephthalate such as Myler (trade name), polyimide such as Kapton (trade name), or the like. In FIG. 5, the shields 27a and 27b are presented as discs. Nonetheless, they may be rectangular instead, or may have any other desirable shape.

The shields 27a and 27b are of the type that adheres to the thick member 26 when they are pressed onto the thick member 26 in the direction of arrows C. The shields 27a and 27b may be bonded to the surface of the thick member 26 by applying appropriate adhesive. Once the shields 27a and 27b are adhered to the sides of the thick member 26, a sample chamber 28 is provided. The sample chamber 28 is watertight and shielded from outside.

Before both shields 27a and 27b are adhered to the thick member 26, an ion-exchange film 29, or sample 17, is placed in the sample chamber 28 in the present embodiment. Then, the shields 27a and 27b are adhered to the thick member 26, thus closing the sample chamber 28. Note that the ion-exchange film 29, which is used as sample 17, is a part of the ion-exchange film to be used in a fuel cell, which is larger and shaped differently.

The ion-exchange film 29 held in the sample chamber 28 remains wetted, or is maintained at humidity of 100%. This is identical to the condition in which the ion-exchange film 29 is used in practice as a component of a fuel cell.

The sample chamber assembly 24 that defines the sample chamber 28 is clamped between the heat plates 22a and 22b. Hence, the air in the chamber 28 is heated as the plates 22a and 22b radiate heat. The ion-exchange film 29 placed in the chamber 28 is therefore heated.

When used as a component of a fuel cell, the ion-exchange film 29 is heated as an electrochemical reaction proceeds in the fuel cell. Thus, the heat plates 22a and 22b can heat the ion-exchange film 29 to set the ion-exchange film in the same condition the film 29 is actually used. If used in a fuel cell, the ion-exchange film 29 may be heated to a temperature ranging from room temperature to 100° C. In view of this, it is desirable to heat the ion-exchange film 29 to such a temperature in the sample chamber 28.

The heat plates 22a and 22b have a through hole 31 each, in their center parts. One of the holes 31 allows passage of the X-rays being applied to the ion-exchange film 29. The other hole 31 allows passage of the scattered radiation emanating from the ion-exchange film 29.

The reading device 2 shown in FIG. 2 has a reading unit 32 and a processing unit 33. The reading unit 32 scans an object with, for example, a laser beam, in X direction (i.e., main scanning direction) and Y direction (i.e., sub-scanning direction). That is, the unit 32 excites the object, or a storage phosphor plate 12, with the laser beam, thereby reading an energy latent image from the storage phosphor plate 12.

The processing unit 33 has a CPU (i.e., Central Processing unit) 34, a RAM (i.e., Random Access Memory) 36, and a ROM (i.e., Read Only Memory) 37. The CPU 34 functions as a control unit and operation unit. The RAM 36 serves as a temporary storage area such as a temporary file or the like. The ROM 37 works as a storage area for fixed data that need not be altered at all. A bus 39 connects the CPU 34, RAM 36 and ROM 37 to one another, which is an address bus or a data bus.

The processing unit 33 has a memory 38 which comprises an external storage medium such as a hard disk or a CD (i.e., Compact Disc). The memory 38 has various storage areas, including a storage area for storing the program software that is used to read data. The output terminal of the reading unit 32 is connected to an X-ray intensity calculating circuit 41.

The X-ray intensity calculating circuit 41 receives a signal output from the reading unit 32. In accordance with the signal the circuit 41 finds the intensity of the X-rays that have served to form the energy latent image on the storage phosphor plate 12. The CPU 34 monitors, at all times, the coordinate position on the storage phosphor plate 12, at which the reading unit 32 is reading data from the plate 12. The CPU 34 and the X-ray intensity calculating circuit 41 cooperate, calculating the scattering angle and intensity of the scattered radiation emanating from the sample 17 shown in FIG. 3, i.e., ion-exchange film 29, from the latent image data stored in the storage phosphor plate 12.

Referring again to FIG. 2, an image display 43 and a printer 46 are connected to the processing unit 33 by a video data generating circuit 42 and a print data generating circuit 44, respectively. The image display 43 may be a CRT (i.e., Cathode Ray Tube) display, a flat panel display, or the like. The flat panel display may be a planar display such as a liquid crystal display, EL (i.e., Electro Luminescence) display, a plasma display, or the like. The printer 46 may be one selected from various types including an ink-coating type, an electrostatic transfer type, and the like.

A method of evaluating organic samples, or ion-exchange film, which employs the X-ray measuring apparatus described above, will be explained.

First, water is introduced into the sample chamber 28 of the sample chamber assembly 24 depicted in FIG. 5. Then, the ion-exchange film 29, or sample, is placed in the sample chamber 28 and clamped between the heat plates 22a and 22b. Thus, the ion-exchange film 29 is held at a prescribed position in the sample holder 11 illustrated in FIG. 1.

The method of evaluating organic samples was carried out when the room temperature was 26° C. The temperatures of the water and ion-exchange film 29, both in the sample chamber 28, were first set at 50° C. and then changed to 60° C., 70° C., 80° C., 90° C., 100° C., 110° C., 120° C., and finally to 130° C., by applying the heat generated by the heat plates 22a and 22b.

The sample was evaluated at each of the temperatures specified above, by means of the X-ray small-angle optical device 1 and reading device 2 shown in FIG. 1 and FIG. 2, respectively. More precisely, the X-ray source 3 was driven and emitted an X-ray. The X-ray was applied to the ion-exchange film 29. Irradiated with the X-ray, the film 29 generated scattered radiation. The scattered radiation irradiated the storage phosphor plate 12. Irradiated with the radiation, the storage phosphor plate 12 stored an energy latent image.

To be more specific, the X-ray source 3 emits an X-ray of high intensity, which is point-focused as shown in FIG. 3. The con-focal mirror 6 focuses the X-ray at the focus f. The first slit 7 and second slit 8, which constitute a double slit, render the focused X-ray stable. The third slit 9 prevents the parasitic scattered radiation generated at the second slit 8 from irradiating the ion-exchange film 29 or the storage phosphor plate 12.

Figure 6:
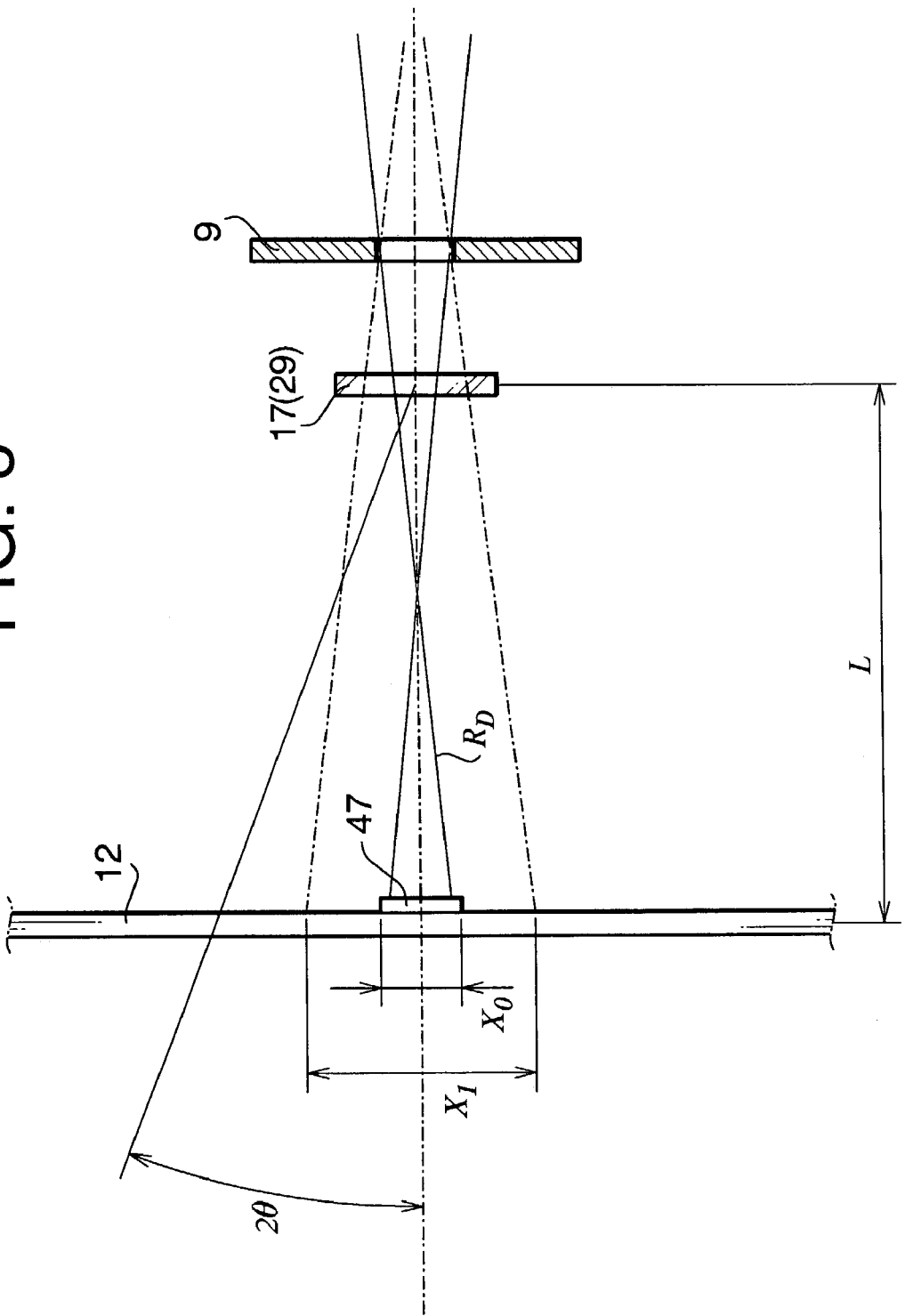
FIG. 6 is a schematic diagram illustrating how the two-dimensional X-ray detector is exposed to scattered radiation in the X-ray small-angle optical device shown in FIG. 1.

The X-rays passes through the third slit 9 and is applied to the ion-exchange film 29. Then, radiation scattered at an angle $2\theta$ determined by the molecular structure of the film 29 is generated as shown in FIG. 6. The scattered radiation has intensity that depends on the molecular structure of the ion-exchange film 29. An energy latent image corresponding to the intensity of the scattered radiation is stored in that part of the storage phosphor plate 12 which has been irradiated with the scattered radiation.

As shown in FIG. 6, a direct beam stopper 47 is mounted on the region X0 of the storage phosphor plate 12, toward which a direct beam $R_D$ is applied. The stopper 47 prevents the direct beam $R_D$ from directly illuminating the storage phosphor plate 12. In FIG. 6, X1 denotes the region in which the parasitic scattered radiation generated at the second slit 8 reaches the storage phosphor plate 12, not blocked by the third slit 9.

In the regions X0 and X1 of the storage phosphor plate 12, the scattered radiation from the ion-exchange film 29 cannot be measured, bothered by the direct beam and the parasitic scattered radiation. Hence, the region of small angle 2θ, where the X-ray small-angle optical device 1 according to this embodiment can measure X-rays, lies outside the region X1 of FIG. 6. The small angle ranges from 0.1° to 5°, preferably from 0.1° to 4°.

To measure scattered radiation in such a small-angle region, it is necessary to narrow the slits 7, 8 and 9, thereby to render the X-ray extremely thin, and to lengthen the camera length L. In view of the above, the ordinary X-ray measuring method using a wide-angle goniometer cannot measure the X-ray. Since the X-ray is made thin, it has low intensity when it reaches the ion-exchange film 29. It therefore takes a long time to measure the X-ray.

In the present embodiment, the con-focal mirror 6 focuses the X-ray emitted from the X-ray source 3 as illustrated in FIG. 3. Moreover, the X-ray from the X-ray source 3 is a point-focused one. That is, the X-ray applied to the ion-exchange film 29 is more intense than in the conventional X-ray measuring apparatus. With this embodiment it is possible to apply scattered radiation of sufficient intensity to the storage phosphor plate 12, within a short time, for example about 20 minutes. In other words, the X-ray measuring apparatus according to the embodiment can measure the X-ray within such a short time.

Figure 8A:
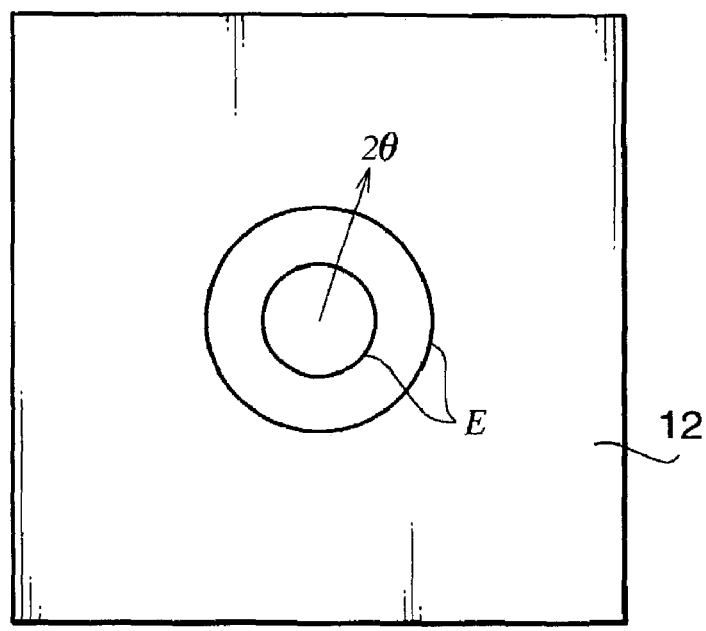
FIG. 8A is a diagram depicting a two-dimensional scattering profile formed on the two-dimensional X-ray detector when the molecular structure of the sample has disturbance.
Figure 8B:
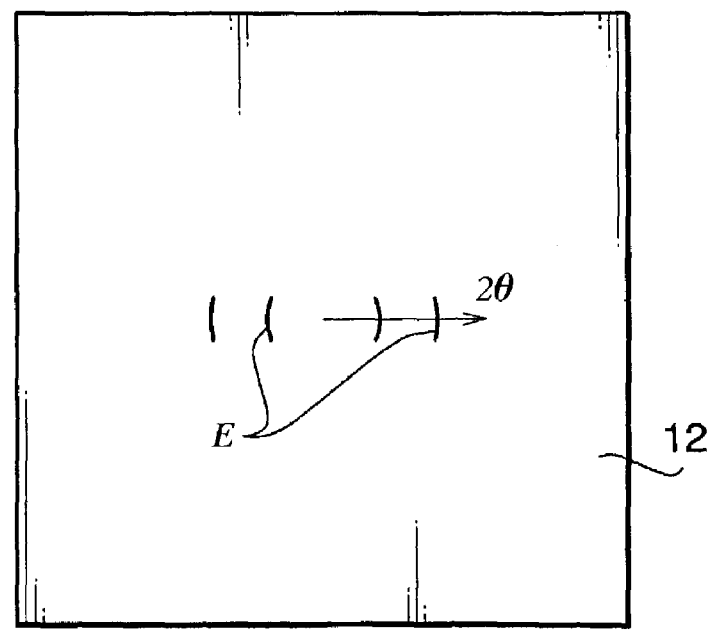
FIG. 8B is a diagram depicting a two-dimensional scattering profile formed on the two-dimensional X-ray detector when the molecular structure of the sample has no disturbance.

When the small-angle scattered radiation is measured at one temperature, such a two-dimensional scattering profile E as depicted in FIG. 8A or FIG. 8B is formed storage phosphor plate 12, as an energy latent image.

The image display 43 or the printer 46, either shown in FIG. 2, displays the two-dimensional scattering profile E of FIG. 8. The profile E displayed or printed is examined to evaluate the ion-exchange film 29. Thus, it is possible to evaluate the regularity of molecular structure, more precisely the alignment of the straight chains 54 and side chains 56 in each molecule.

As described above with reference to FIG. 1 and FIG. 3, a latent image pertaining to the ion-exchange film 29 is formed in the storage phosphor plate 12 by exposing the plate 12 to the scattered radiation at one of measuring temperatures. Then, the storage phosphor plate 12 is removed from the X-ray small-angle optical device 1 and set at a reading position prescribed with respect to the reading unit 32 of the reading device 2 shown in FIG. 2. The reading unit 32 scans the latent image, measuring the scattering angle (2θ) and intensity of the scattered radiation from the two-dimensional scattering profile E shown in FIG. 8A or 8B.

Figure 7:
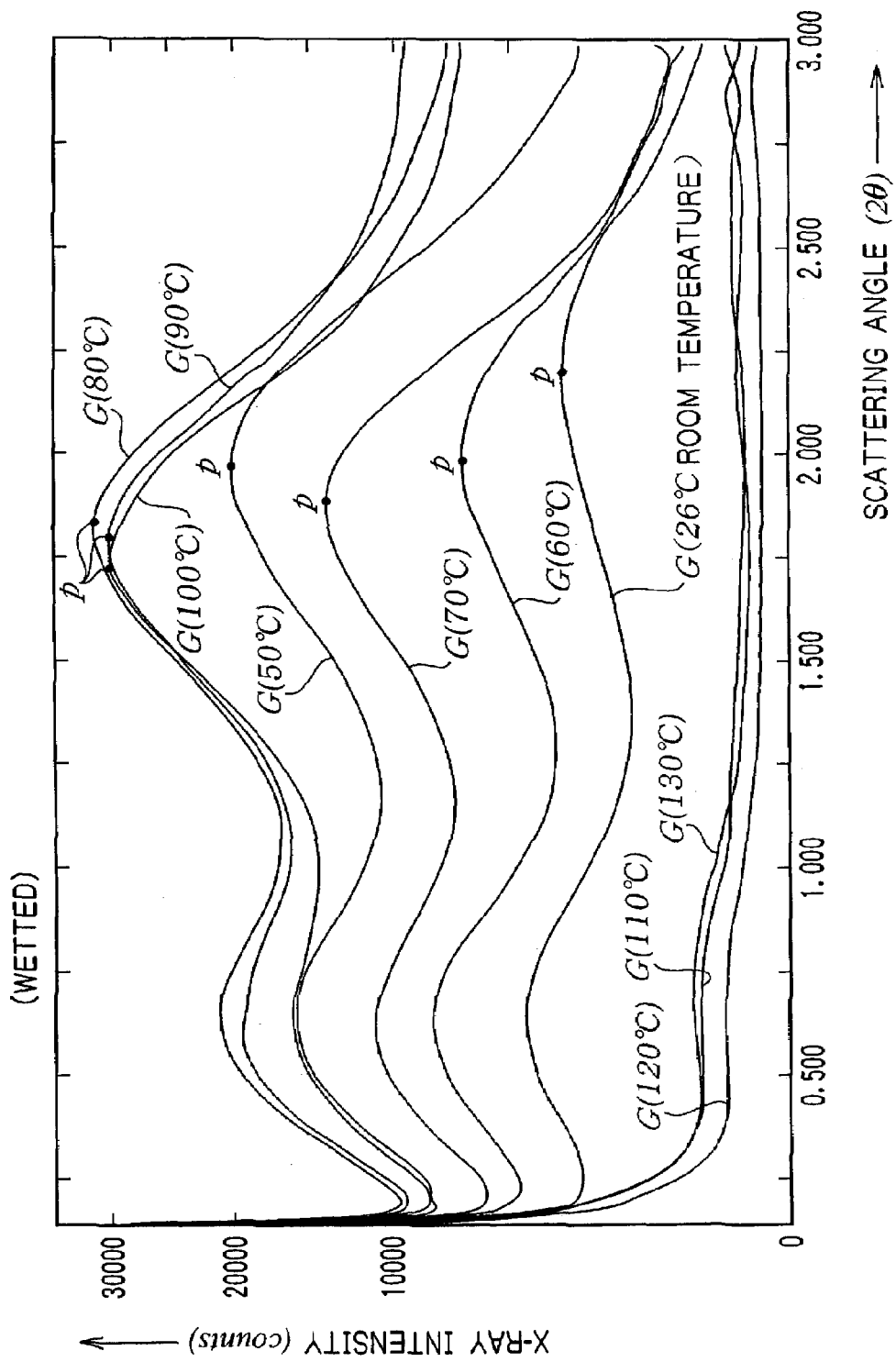
FIG. 7 is a graph representing small-angle scattering curbs read by the reading device shown in FIG. 2.

The CPU 34 shown in FIG. 2 stores the scattering angel (2θ) and intensity of the scattered radiation, thus measured, at a predetermined storage area in the RAM 36 or memory 38, in the form of, for example, a data table. The image display 43 and the printer 46 can display and print the data table, as such small-angle scattered curves G as shown in FIG. 7. In the graph of FIG. 7, the scattering angle (2θ) is plotted on the abscissa, and the X-ray intensity on the ordinate.

Assume that the ion-exchange film 29 is examined, while held as shown in FIG. 1 at room temperature (26° C.). Then, we have the small-angle scattering curve G(26° C.) illustrated in FIG. 7. Next, the temperature of the ion-exchange film 29 is changed to 50° C., 60° C., 70° C., 80° C., 90° C., 100° C., 110° C., 120° C. and 130° C., by the control of the temperature control circuit 23 shown in FIG. 1, and the ion-exchange film 29 is examined at these temperatures by the X-ray small-angle optical device 1 of FIG. 1. As a result, the two-dimensional scattering profile E shown in FIGS. 8A and 8B is formed in the storage phosphor plate 12. The reading device 2 reads the scattering profile E from the plate 12. The CPU 34 processes the data representing the scattering profile E, generating the data items that represent the small-angle scattering curves G(50° C.), G(60° C.), G(70° C.), G(80° C.), G(90° C.), G(100° C.), G(110° C.), G(120° C.) and G(130° C.), all shown in FIG. 7.

The CPU 34 calculates peaks P at the temperatures specified above, respectively, from the small-angle scattering curves G(26° C.) to G(130° C.), for the scattering angle 2θ. The CPU 34 calculates the X-ray intensities at these peaks from the intensities that the scattered radiation has at the temperatures specified above. The CPU 34 causes the image display 43 or the printer 46 to display or print the peak P at each temperature, on the corresponding small-angle scattering curve G, in such a dot-matrix form as is illustrated in FIG. 7.

Figure 10:
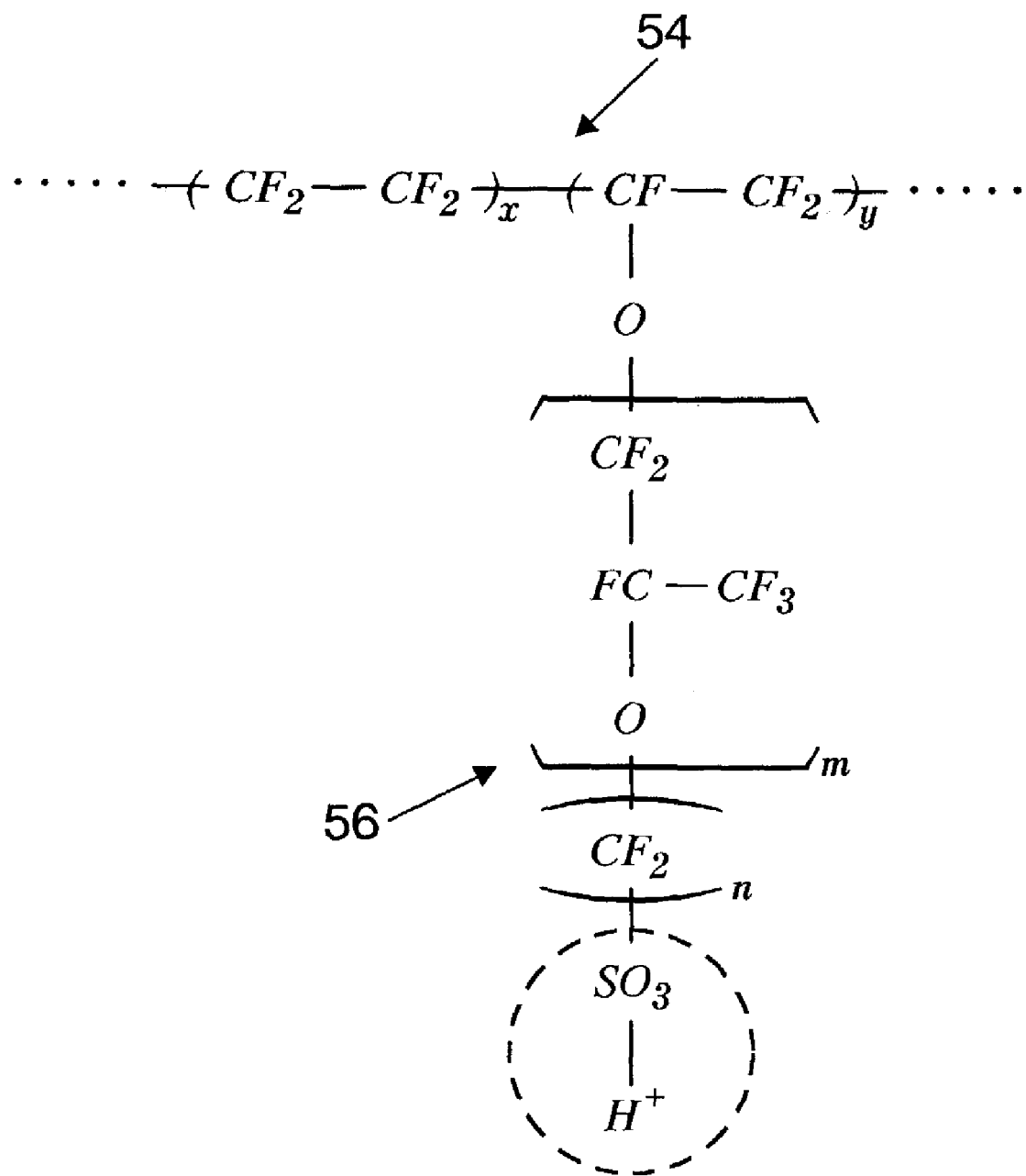
FIG. 10 is a structural formula of the ion-exchange film.
Figure 11:
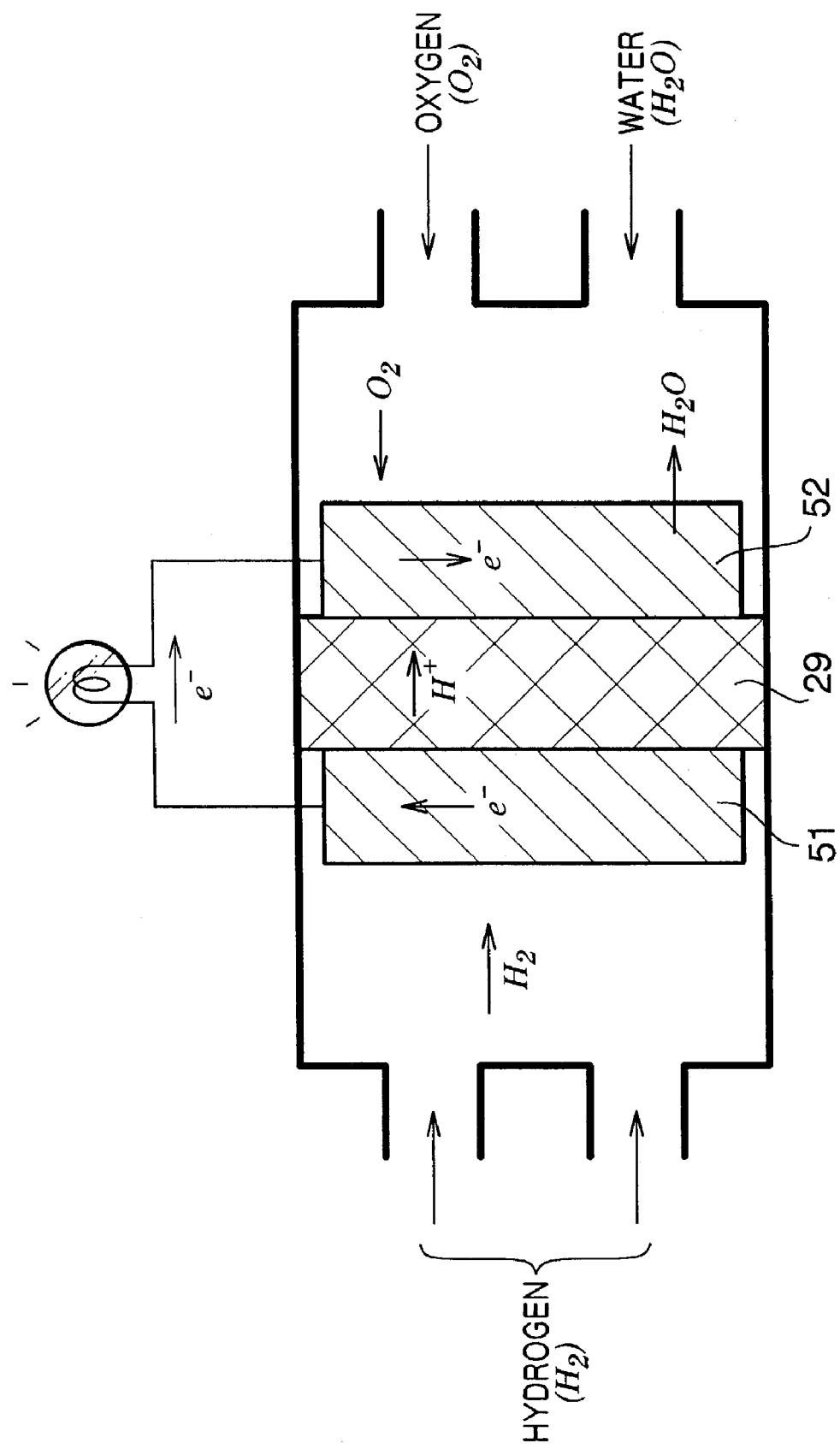
FIG. 11 is a schematic representation of a fuel cell comprising the fuel cell.

Any person who observes the graph of FIG. 7 can easily recognize how the position of the peak changes and how the X-ray intensity at the peak changes as the temperature of the ion-exchange film 29 is varied while the film 29 remains at the humidity of 100%. The peak position and the X-ray intensity at the peak change as the molecular structure of the ion-exchange film 29, shown in FIG. 9C and FIG. 10, changes due to the change in the temperature of the film 29 maintained at the humidity of 100%. Thus, the observer can determine the molecular structure of the ion-exchange film 29 by evaluating the change in the position of the peak on the small-angle scattering curve G (FIG. 7) or the change in the X-ray intensity at the peak, or both.

Once incorporated into a fuel cell, the ion-exchange film 29 is used at a temperature ranging from room temperature to a higher temperature but less than 100° C. It is used most frequently at 80° C. to 90° C. The molecular structure that the ion-exchange film 29 has while it is acting in the fuel cell can be determined by referring to the small-angle scattering curves G(80° C.) and G(90° C.), both presented in FIG. 7. In other words, the performance of the ion-exchange film 29, thus measured, can be evaluated when it is used in practice by referring to the small-angle scattering curves G(80° C.) and G(90° C.).

The inventors hereof believe that, if the positions of the peaks on the small-angle scattering curves G shown in FIG. 7 are known, the molecular structure of the ion-exchange film 29 can be determined. If the X-ray intensities at the peaks are known, the number of side chains 56 and the regularity of the molecular structure of the ion-exchange film 29 can be determined.

As may be clear from the foregoing, the X-ray measuring apparatus comprising the X-ray small-angle optical device 1 shown in FIG. 1 and the reading device 2 shown in FIG. 2 can accurately evaluate the performance, for example, ion-exchanging ability of the ion-exchange film 29 in the condition of actual use. Thus, the method according to this embodiment can evaluate ion-exchange films set in such a use condition, whereas the conventional method, such as NMR-measuring method and IR-measuring method, can hardly evaluate ion-exchange film set in the use condition.

In particular, according to this embodiment, the X-ray source 3 provided in the X-ray small-angle optical device 1 (shown in FIG. 1) can emit X-rays of high intensity. This is because the X-ray source 3 comprises a rotor target that incorporates a cooling unit. Further, the con-focal mirror 6 focuses the X-ray, which irradiates the ion-exchange film 29. Therefore, the small-angle scattering measuring can be performed on the ion-exchange film 29 within a very short time.

The ion-exchange film 29 is maintained in wetted state and at a high temperature close to 100° C. If it takes a long time to perform the small-angle scattering measuring, the state of the ion-exchange film 29 and the humidity ambient to the film 29 will change before the measuring is finished. This may render it no longer possible to achieve a reliable in-situ measuring. To perform a reliable in-situ measuring, the X-ray applied to the ion-exchange film 29 is intensified in this embodiment, shortening the measuring time. Thus, a high-precision in-situ measuring is accomplished in the present embodiment.

(Second Embodiment)

In the first embodiment described above, the performance of the ion-exchange film 29 is evaluated from three factors, i.e., the difference between the positions of the peaks on the small-angle scattering curves G shown in FIG. 7, the difference between the X-ray intensities at these peaks, and the two-dimensional scattering profiles E shown in FIG. 8. In the second embodiment of the invention, the performance of the film 29 can be evaluated on the basis of only one or two of the three factors.

(Third Embodiment)

In the embodiments described above, one ion-exchange film 29 is set in different conditions, the small-angle scattering curves G and two-dimensional scattering profiles E for the respective conditions are obtained, and the change in the molecular structure of the ion-exchange film 29 is determined, thus evaluating the performance of the film 29.

Instead, a plurality of ion-exchange films whose molecular structures are unknown are subject to X-ray small-angle measuring in the third embodiment of the present invention. Small-angle scattering curves G and two-dimensional scattering profiles E are thereby obtained. From the curves G and the profiles E, the different molecular structures of the respective ion-exchange films can be determined. In the third embodiment, the ion-exchange films can be measured while maintained at the same temperature.

Moreover, the small-angle scattering curves G for a standard ion-exchange film may be stored in the memory 38 of the processing unit 33 shown in FIG. 2 and may be compared with the small-angle scattering curves G actually obtained of an ion-exchange film. Thus, the ion-exchange film is evaluated in terms of its performance.

(Fourth Embodiment)

In the embodiments described above, small-angle X-ray measuring is carried out, while the ion-exchange film 29 remains immersed in water and, thus, wetted at humidity of 100%. Nonetheless, the ion-exchange film 29 may be immersed in liquid other than water. Further, the film may be subjected to the measuring, while remaining dried.

(Fifth Embodiment)

In the embodiments described above, the X-ray source is a point-focus source that comprises a rotor target and the con-focal mirror is used as X-ray focusing means. The fifth embodiment may use an X-ray focusing means other than a con-focal mirror, or may not use the X-ray focusing means at all as the case may be. Further, a line-focus X-ray source may be used in some cases. Still further, a target other than a rotor target may be used in some cases.

Furthermore, a monochromator may be arranged on the X-ray path extending from the X-ray source 3 to the ion-exchange film 29, preferably on the X-ray path extending from the X-ray source 3 to the con-focal mirror 6 in FIG. 3. Thus, the X-ray being applied to the ion-exchange film 29 is changed to a monochromic beam, such as a $CuK\alpha$ beam. Alternatively, the X-ray focusing means equivalent to the con-focal mirror 6 may be a monochromator made of single crystal. If this is the case, it can focus the incident X-ray and change the same to a monochromic beam at the same time.

(Sixth Embodiment)

In the embodiments described above, the object to be evaluated is an ion-exchange film. The sixth embodiment is designed to evaluate organic samples other than ion-exchange films. The samples that the sixth embodiment may evaluate are, for example, macromolecular organic materials, genome pharmaceutical substances, and the like.

(Seventh Embodiment)

The embodiments described above use an optical system having three slits. The seventh embodiment of the invention may use an X-ray small-angle optical device of any other configuration. Moreover, the seventh embodiment may comprise a sample holder that differs in structure from the sample holder 11 shown in FIG. 5.

Various embodiments of the present invention have been described. Nevertheless, this invention is not limited to them. Rather, various changes and modifications can be made, within the scope of the claims set forth hereinafter.

What is claimed is:

1. A method of evaluating the performance of an ion-exchange film, comprising the steps of:

obtaining small-angle scattering curves for at least one ion-exchange film, by means of an X-ray measuring apparatus which is configured to detect X-rays scattered at small angles with respect to the axis of an X-ray applied to the ion-exchange film;

wherein each small-angle scattering curve is obtained, each curve while the film remains in a different condition; and finding a difference between the positions of peaks on the small-angle scattering curves and/or a difference between the X-ray intensities at the peaks, and evaluating the performance of the ion-exchange film from the determined difference.

2. The method according to claim 1, further comprising the steps of:

obtaining small-angle scattering curves for a plurality of ion-exchange films; and finding a difference between the positions of peaks on the small-angle scattering curves and/or a difference between the X-ray intensities at the peaks.

3. The method according to claim 1, wherein the step of obtaining small-angle scattering curves is performed while the ion-exchange film remains held in a watertight sample chamber, together with liquid.

4. The method according to claim 1, wherein the step of obtaining small-angle scattering curves is performed while the ion-exchange film remains held in a watertight sample chamber, together with liquid, and while a temperature in the sample chamber remains at a value adjusted.

5. The method according to claim 4, wherein the temperature in the sample chamber is adjusted to a value at which the ion-exchange film is used in practice.

6. The method according to claim 5, wherein the step of obtaining small-angle scattering curves is performed on the ion-exchange film by means of a two-dimensional X-ray detector.

7. The method according to claim 6, wherein the X-ray measuring apparatus has X-ray focusing means which is arranged on a propagation path of the X-ray applied to the ion-exchange film.

8. The method according to claim 7, wherein the X-ray focusing means is a con-focal mirror.

9. The method according to claim 8, wherein the X-ray measuring apparatus further has a point-focus X-ray source.

10. A method of evaluating the performance of an organic sample, comprising the steps of:
    obtaining small-angle scattering curves for at least one organic sample, by means of an X-ray measuring apparatus which is configured to detect X-rays scattered at small angles with respect to the axis of an X-ray applied to the organic sample;
    wherein each small-angle scattering curve is obtained while the sample remains in a different condition; and
    finding a difference between the positions of peaks on the small-angle scattering curves and/or a difference between the X-ray intensities at the peaks, end
    evaluating the performance of the organic sample from the determined difference.

11. The method according to claim 10, further comprising the steps of:
    obtaining small-angle scattering curves for a plurality of organic samples; and
    finding a difference between the positions of peaks on the small-angle scattering curves and/or a difference between the X-ray intensities at the peaks.

12. The method according to claim 10, wherein the step of obtaining small-angle scattering curves is performed while the organic sample remains held in a watertight sample chamber, together with liquid.

13. The method according to claim 10, wherein the step of obtaining small-angle scattering curves is performed while the organic sample remains held in a watertight sample chamber, together with liquid, and while a temperature in the sample chamber remains at a value adjusted.

14. The method according to claim 13, wherein the temperature in the sample chamber is adjusted to a value at which the organic sample is used in practice.

15. The method according to claim 14, wherein the step of obtaining small-angle scattering curves is performed on the organic sample by means of a two-dimensional X-ray detector.

16. The method according to claim 15, wherein the X-ray measuring apparatus has X-ray focusing means which is arranged on a propagation path of the X-ray applied to the organic sample.

17. The method according to claim 16, wherein the X-ray focusing means is a con-focal mirror.

18. The method according to claim 17, wherein the X-ray measuring apparatus further has a point-focus X-ray source.

19. An X-ray measuring apparatus comprising:
    a small-angle X-ray optical system which is configured to detect X-rays scattered at small angles with respect to the axis of an X-ray applied to a sample;
    first storage means for storing small-angle scattering curves obtained by using the small-angle X-ray optical system;
    second storage means for storing small-angle scattering curves for a standard sample;
    display means for displaying the small-angle scattering curves stored in the first storage means and the small-angle scattering curves stored in the second storage means, either at the same time or at different times; and
    a sample chamber which is configured to allow passage of X-rays, to contain liquid in watertight fashion and to hold the sample in the liquid.

20. The X-ray measuring apparatus according to claim 19, further comprising sample-temperature adjusting means for adjusting the temperature in the sample chamber.

21. An X-ray measuring apparatus comprising:
    a small-angle X-ray optical system which is configured to detect X-rays scattered at small angles with respect to the axis of an X-ray applied to a sample;
    means for calculating the positions of peaks on the small-angle scattering curves obtained by using the small-angle X-ray optical system;
    means for displaying the position of peaks thus calculated together with the small-angle scattering curves; and
    a sample chamber which is configured to allow passage of X-rays, to contain liquid in watertight fashion and to hold the sample in the liquid.

22. The X-ray measuring apparatus according to claim 21, further comprising sample-temperature adjusting means for adjusting the temperature in the sample chamber.

* * * * *